US011654229B2

(12) United States Patent
Sloan

(10) Patent No.: US 11,654,229 B2
(45) Date of Patent: May 23, 2023

(54) WOUND IRRIGATION DEVICE

(71) Applicant: Indiana University Research and Technology Corporation, Indianapolis, IN (US)

(72) Inventor: Brian Sloan, Zionsville, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 729 days.

(21) Appl. No.: 16/085,806

(22) PCT Filed: Mar. 17, 2017

(86) PCT No.: PCT/US2017/023051
§ 371 (c)(1),
(2) Date: Sep. 17, 2018

(87) PCT Pub. No.: WO2017/161323
PCT Pub. Date: Sep. 21, 2017

(65) Prior Publication Data
US 2020/0297916 A1    Sep. 24, 2020

Related U.S. Application Data

(60) Provisional application No. 62/310,217, filed on Mar. 18, 2016.

(51) Int. Cl.
*A61M 3/02* (2006.01)
*B05B 15/16* (2018.01)
(Continued)

(52) U.S. Cl.
CPC ........ *A61M 3/0279* (2013.01); *A61M 3/0245* (2013.01); *A61M 3/0262* (2013.01);
(Continued)

(58) Field of Classification Search
CPC .. A61M 39/22; A61M 3/0262; A61M 3/0279; A61M 3/0233; A61M 31/00;
(Continued)

(56) References Cited

U.S. PATENT DOCUMENTS 3,688,766 A * 9/1972 Kempel .............. A61M 3/0262
604/212
3,754,553 A * 8/1973 Hewitt ................ A61M 3/0262
604/212
(Continued)

FOREIGN PATENT DOCUMENTS

WO    WO-8504108 A1 *  3/1985    .......... A61M 3/0262
WO    WO-9212758 A1 *  8/1992    ............ A61M 31/00
(Continued)

OTHER PUBLICATIONS

International Preliminary Report on Patentability received for PCT Patent Application No. PCT/US2017/023051, dated Sep. 27, 2018, 11 pages.
(Continued)

*Primary Examiner* — Erich G Herbermann
*Assistant Examiner* — Seth Han
(74) *Attorney, Agent, or Firm* — Hartman Global IP Law; Gary M. Hartman; Domenica N. S. Hartman

(57) ABSTRACT

A wound irrigation device including a container with an opening along the outer surface of the container and a nozzle assembly coupled to the container and configured to selectively allow the liquid to exit the container when pressure is applied to the container.

15 Claims, 5 Drawing Sheets

(51) Int. Cl.
  *A61M 39/22* (2006.01)
  *B05B 11/04* (2006.01)
  *B05B 11/00* (2023.01)
(52) U.S. Cl.
  CPC ......... *A61M 39/22* (2013.01); *B05B 11/0056* (2013.01); *B05B 11/0072* (2013.01); *B05B 11/047* (2013.01); *B05B 15/16* (2018.02)
(58) Field of Classification Search
  CPC ............... A61M 35/003; A61M 39/24; A61M 2039/066; B05B 11/0056; B05B 11/007; B05B 11/0072; B05B 11/047; B05B 15/16; A61J 9/08; B65D 47/2018; B65D 47/2031; B65D 43/162; B65D 43/16
  USPC ....................................................... 604/410
  See application file for complete search history.

(56) References Cited

U.S. PATENT DOCUMENTS

| | | | |
|---|---|---|---|
| 4,222,379 A | 9/1980 | Smith | |
| 4,357,937 A | 11/1982 | Burrell, Jr. et al. | |
| 4,692,140 A | 9/1987 | Olson | |
| 4,769,003 A | 9/1988 | Stamler | |
| 5,133,701 A | 7/1992 | Han | |
| 5,441,174 A | 8/1995 | Sperry | |
| 5,496,290 A | 3/1996 | Ackerman | |
| 5,795,324 A | 8/1998 | Morse | |
| 5,830,197 A | 11/1998 | Rucinski | |
| 5,941,859 A | 8/1999 | Lerman | |
| 6,050,981 A | 4/2000 | Lampropoulos et al. | |
| 6,293,929 B1 | 9/2001 | Smith et al. | |
| 6,402,724 B1 | 6/2002 | Smith et al. | |
| 6,427,874 B2 * | 8/2002 | Brown ............... B65D 47/2031 | 222/185.1 |
| 6,558,344 B2 | 5/2003 | McKinnon et al. | |
| 6,623,257 B2 | 9/2003 | Taniguchi | |
| 6,872,197 B1 * | 3/2005 | Witowski ............... B32B 15/08 | 604/113 |
| 7,621,897 B1 * | 11/2009 | Berke ................... A61F 9/0026 | 604/295 |
| 7,959,617 B2 | 6/2011 | Rucinski | |
| 8,002,757 B1 * | 8/2011 | Schultz .................. A61B 90/05 | 604/289 |
| 8,021,346 B2 | 9/2011 | Rucinski | |
| 8,747,372 B1 | 6/2014 | Schultz | |
| 9,649,259 B2 * | 5/2017 | Burnett ..................... A61J 9/00 | |
| 2001/0037095 A1 | 11/2001 | Rucinski | |
| 2004/0004082 A1 * | 1/2004 | Lee ....................... B65D 1/0292 | 220/703 |
| 2004/0116903 A1 | 6/2004 | Osman | |
| 2005/0090777 A1 | 4/2005 | Carter | |
| 2005/0124946 A1 * | 6/2005 | Landau ............... A61M 3/0262 | 604/317 |
| 2005/0148958 A1 * | 7/2005 | Rucinski ............. A61M 3/0279 | 604/290 |
| 2008/0065001 A1 | 3/2008 | DiNucci et al. | |
| 2011/0245786 A1 | 10/2011 | Hulse | |
| 2011/0284557 A1 * | 11/2011 | Hayakawa ........... B65D 1/0276 | 220/601 |
| 2011/0319840 A1 * | 12/2011 | Hair .................... A61M 3/0262 | 604/151 |
| 2012/0035559 A1 | 2/2012 | Rucinski | |

FOREIGN PATENT DOCUMENTS

WO    2008/144435 A1    11/2008
WO    WO-2008144435 A1 *  11/2008   .......... A61M 35/003

OTHER PUBLICATIONS

International Search Report and Written Opinion received for PCT Patent Application No. PCT/US2017/023051, dated Jun. 12, 2017, 11 pages.

Singer, A.J. et al. (Feb. 24, 1994). Pressure Dynamics of Varies Irrigation Techniqes Commonly Used in the Emergency Department. Ann Emerg Med 24:36-40. p. 36.

* cited by examiner

WOUND IRRIGATION DEVICE

CROSS REFERENCE TO RELATED APPLICATIONS

This application is a national phase filing of PCT International Application Serial No. PCT/US2017/023051, filed Mar. 17, 2017, which claims priority to U.S. Provisional Application No. 62/310,217, which is entitled "WOUND IRRIGATION DEVICE," and was filed on Mar. 18, 2016, the entire disclosures of which are expressly incorporated herein by reference in their entireties.

FIELD OF THE DISCLOSURE

The present invention relates generally to an irrigation device, and more particularly, to a wound irrigation device.

BACKGROUND

Wound irrigation involves the administration of a volume of solution or fluid into a wound to remove loose tissue, to decrease bacterial concentrations within a wound, to remove blood clots and loose debris, and to explore the depths of the wound. Two critical components of wound irrigation are the volume of fluid used for the irrigation and the pressure applied in a fixed stream to effectively remove any contaminants within the wound. The volume necessary to effectively clean a wound is approximately 500 cubic centimeters (cc) with a wide range of scientifically proven volumes from 250 cc to 10,000 cc.

High pressure irrigation can cause damage to tissue and drive pathogens deep into the wound thereby causing infections rather than preventing them. Therefore, the correct amount of pressure needs to be applied when irrigating a wound. Generally, the pressure necessary to effectively clean a wound is between 1.5-10 pounds per square inch (psi).

Several methods for cleaning wounds are in practice in the urgent/emergency care setting. For example, irrigation using sterile water under pressure applied by a syringe attached to a catheter over needle device requires a user/practitioner to first draw an irrigating fluid into a syringe typically holding 20-40 cc of fluid. Once the fluid has been drawn into the syringe, a catheter, typically 18-14 gauge caliber, is secured onto the syringe with a luer lock device. After affixing the catheter to the fluid filled syringe, the user/practitioner inserts the catheter into the wound cavity and forcefully deploys the plunger of the syringe which injects the solution into the wound dislodging debris and reducing the bacterial concentration inside the wound.

Another technique used in urgent/emergency care and urgent care settings includes the use of a sterile bottle of saline that incorporates a splash shield screwed onto the bottle. A 500 cc plastic bottle that is pre-filled with sterile water or saline (commonly available through a variety of medical supply companies) has a cap that is screwed onto the bottle. The cap is removed and replaced with a screw-on device that serves the dual purpose of applying a stream of fluid into the wound and shielding the provider from the splash of the liquid as the wound is irrigated. The above-described system is expensive due to the number of parts required, is heavy to ship and transport within the hospital, and requires a large amount of storage space because of the number of parts required.

In medicine, lacerations must be cleaned prior to closure for three reasons. First, lacerations are contaminated and need to be cleaned to remove foreign material such as organic and inorganic matter including bacteria. Any of these imbedded substances can cause the wound to become infected if the wound is closed before appropriate cleaning has been done. Second, an acceptable cosmetic outcome is desired for patients. Cosmesis can be obtained when the wound has been appropriately cleansed, debrided, and precisely closed using an appropriate closure system. Finally, a wound must be explored prior to closure to ensure there is no tendinous, bony, vascular, muscular, or neurologic injury. If a vital structure is not identified as being injured due to poor wound exploration and irrigation significant morbidity may occur to the patient. Thus, meticulous cleaning of wounds prior to closure is critical for optimal cosmetic outcome, preventing infection, and for maximizing the identification of deep structure injury.

SUMMARY OF THE DISCLOSURE

Illustratively, the wound irrigation device of the present disclosure is a self-contained system where the device can be quickly and effectively filled with potable water or other treatment liquids for irrigation of wounds, and the device can deliver a fluid under pressure into a wound.

According to an embodiment of the present disclosure, a wound irrigation device is provided. The wound irrigation device comprises a collapsible container with a first opening and a second opening, wherein the container can be flattened in a flat configuration; wherein the first opening is positioned along the outer surface of the container and has a valve positioned within the first opening, the valve configured to allow a liquid to enter the container; and wherein the second opening is configured to receive a nozzle assembly removably coupled to the container at the second opening, the nozzle assembly configured to selectively allow the liquid to exit the container when a pressure is applied to the container.

According to yet another embodiment of the present disclosure, the wound irrigation device includes a collapsible container with an first opening along the outer surface of the container, the opening configured to allow a liquid to enter and exit the container; a nozzle assembly coupled to the opening of the container, the nozzle assembly comprising: a lid coupled to the opening and having second opening coaxial with the first opening; and a nozzle coupled to the lid, the nozzle including an insert configured to fit within the second opening of the lid and a guard that extends beyond the second opening, wherein the insert includes a valve; the nozzle assembly having an open configuration and a closed configuration, wherein in the open configuration, the interior of the container is in fluid communication with ambient air via the second opening; wherein in the closed configuration, the insert of the nozzle fits within the second opening of the lid such that the valve can selectively allow liquid to exit the container when pressure is applied to the container.

According to still yet another embodiment of the present disclosure, a method is provided for using a wound irrigation device. The method includes: inserting a liquid into a container through an opening positioned along an outer surface of the container; inverting the container such that the container is positioned above the opening; and applying a pressure onto the outer surface of the container such that the liquid is expelled from the container through the nozzle assembly.

Additional features of the present disclosure will become apparent to those skilled in the art upon consideration of the following detailed description of illustrative embodiments.

BRIEF DESCRIPTION OF THE DRAWINGS

The foregoing aspects and many of the intended features of this disclosure will become more readily appreciated as the same becomes better understood by reference to the following detailed description when taken in conjunction with the accompanying drawings, wherein.

Figure 1:
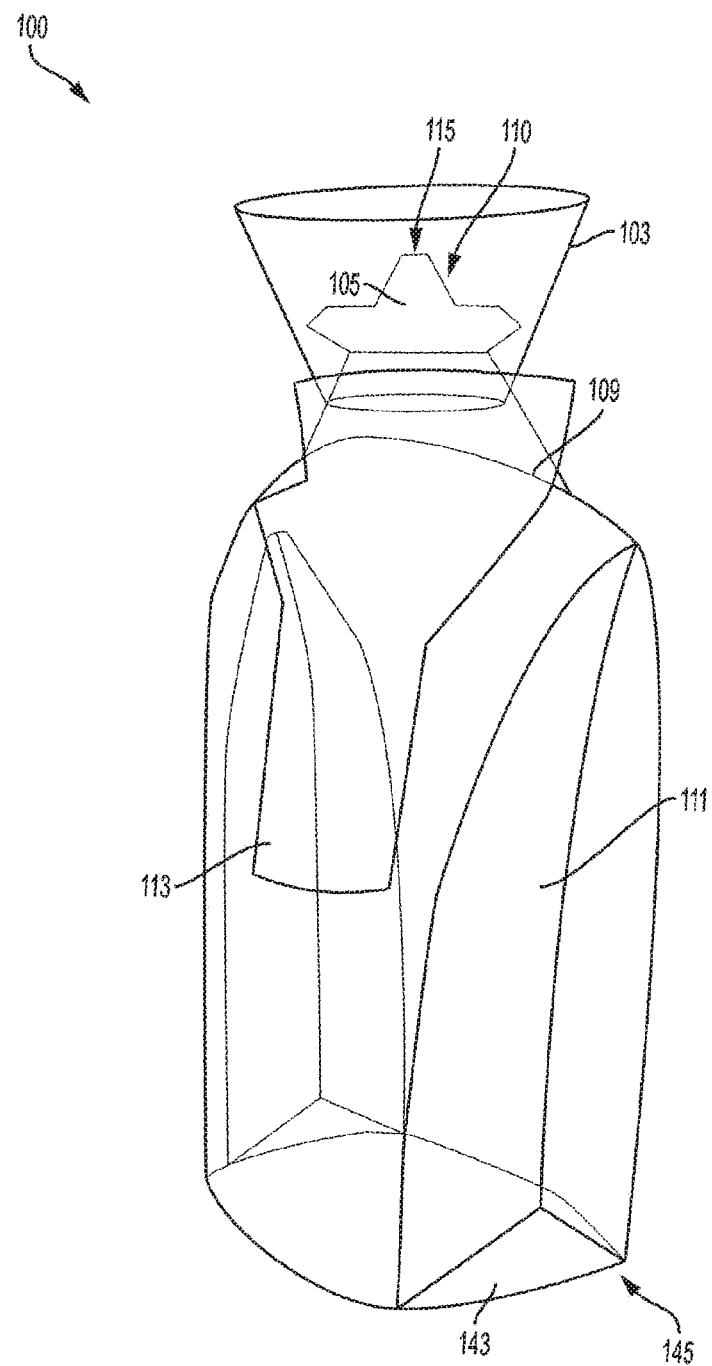
FIG. 1 is a perspective view of a wound irrigation device.
Figure 2:
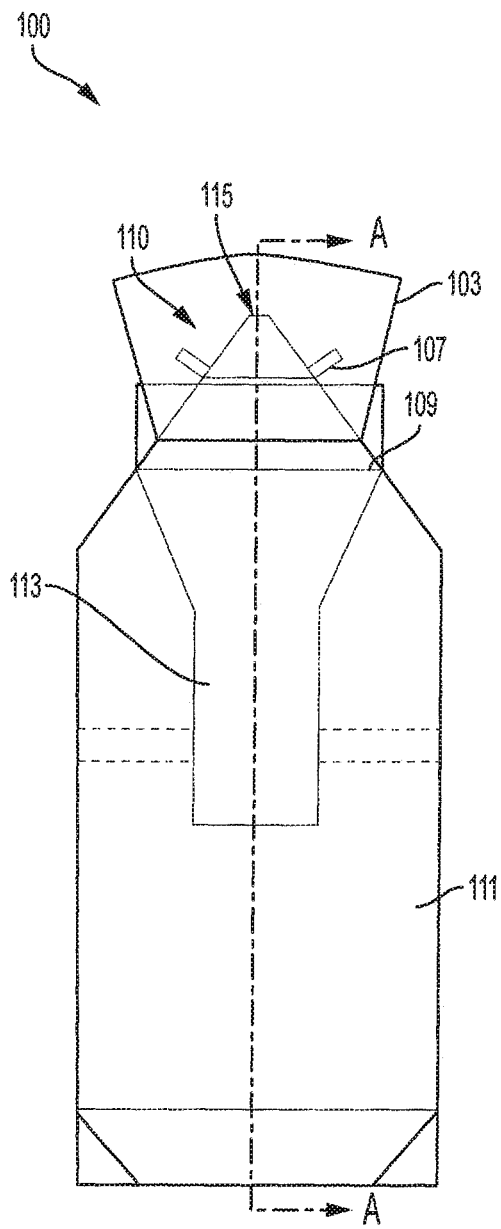
FIG. 2 is a front elevational view of the wound irrigation device of FIG. 1.
Figure 3:
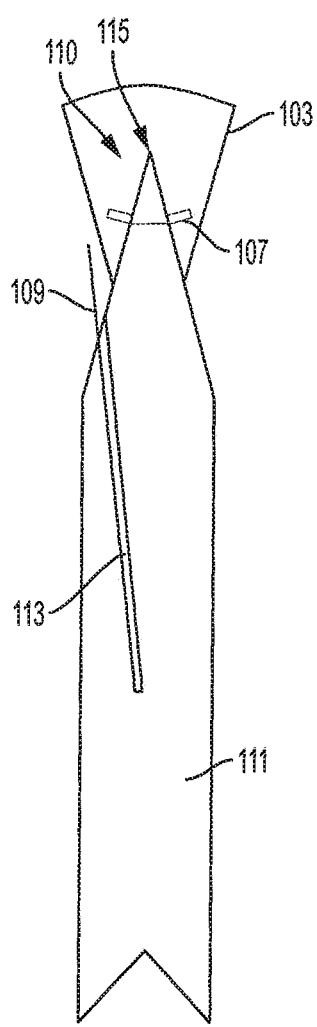
FIG. 3 is a cross-section elevational view of the wound irrigation device of FIG. 2 taken along line A-A.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the disclosure, and such exemplifications are not to be construed as limiting the scope of the disclosure in any manner.

DETAILED DESCRIPTION OF THE DRAWINGS

For the purposes of promoting an understanding of the principals of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. The disclosure includes any alterations and further modifications in the illustrative devices and described methods and further applications of the principles of the disclosure which would normally occur to one skilled in the art to which the disclosure relates.

Referring to FIGS. 1-7, an embodiment of a wound irrigation device 100 is shown. Wound irrigation device 100 includes a container 111 and openings 109, 115 located along an outer surface of container 111.

Container 111 may be made of a flexible material, which allows container 111 to be molded into different configurations to achieve greater storage capacity. For example, each container 111 can be flattened such that a plurality of containers 111 can be stacked on each other. In such a configuration, a greater number of containers 111 can be stored per unit area of storage. This is spatially more efficient as compared to prior embodiments of a wound irrigation device in which more rigid containers (e.g. bottles) are used. In one embodiment, container 111 is made from Bis(2-ethylhexyl)benzene-1,2-dicarboxylate (DEHP). In an alternate embodiment, container 111 may be made from PVC, rubber, or other suitable materials. In an alternate embodiment, container 111 can hold at least 250 cubic centimeters of liquid.

In addition, container 111 includes a self-standing base 145 and a gusset 143. As liquid enters container 111, container 111 expands, and gusset 143 and base 145 provide a foundation upon which container 111 can stand upright.

Openings 109, 115 are positioned on container 111 such that the inside of container 111 is in fluid communication with the ambient air outside container 111. Opening 115 provides an outlet for liquid inside container 111 when wound irrigation 100 is in use as discussed herein. Opening 109 is configured to receive a valve 113. Valve 113 is configured to permit the addition of liquid into container 111, while not allowing liquid to exit container 111 through opening 109 and valve 113. In other words, valve 113 provides a fluid tight seal with the outer surface of container 111 such that liquid cannot exit container 111 at the interface of valve 113 and container 111. In the illustrated embodiment, valve 113 is a one-way valve that extends beyond the outer surface of container 111.

Guard 103 is coupled to container 111 such that the outer rim of guard 103 extends substantially beyond opening 115 of wound irrigation device 100. Guard 103 frictionally engages with container 111. However, it is contemplated that alternative mechanisms for coupling guard 103 and container 111 may be used, for example, fasteners, couplers, etc. In an alternate embodiment, guard 103 is integrally formed with container 111. Guard 103 prevents splash from the liquid, bodily fluids, or other debris from contacting or damaging nozzle assembly 110, which is coupled to container 111 at opening 115 as described in further detail below. Guard 103 can also protect the user from encountering splash from the liquid upon contacting the external surface as well as bodily fluids or other debris from contacting the user.

Figure 4:
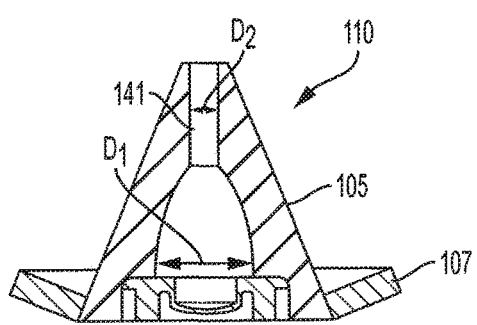
FIG. 4 is a sectional view of a nozzle assembly associated with the wound irrigation device of FIG. 1.
Figure 5:
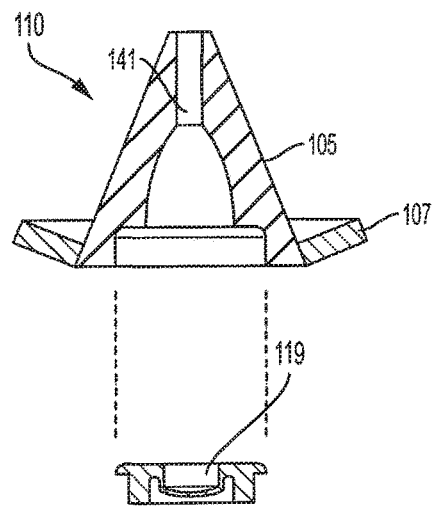
FIG. 5 is an exploded sectional view of the nozzle assembly of FIG. 4 for the wound irrigation device of FIG. 1.
Figure 6:
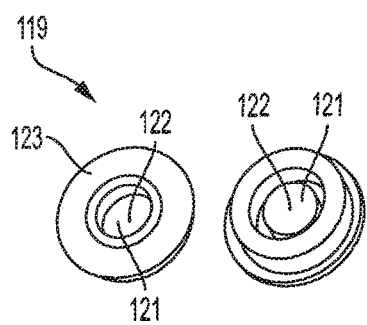
FIG. 6 is a perspective view of an insert that is incorporated with the nozzle assembly of FIGS. 4 and 5.
Figure 7:
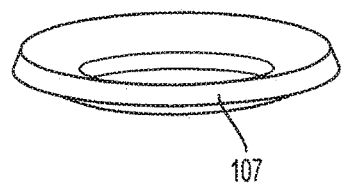
FIG. 7 is a perspective view of a ring that is associated with the nozzle assembly of FIGS. 4 and 5.

Nozzle assembly 110 is operably coupled to container 111 and cooperates with opening 115 to selectively allow fluid to exit container 111. Nozzle assembly 110 includes a nozzle 105, a spacer 107, an insert 119, and a valve 121. As shown in FIGS. 4 and 5, nozzle assembly 110 includes an interior channel 141 that extends though nozzle 105. Interior channel 141 is aligned with opening 115 such that interior channel 141 and opening 115 are coaxial with each other. As such, liquid exiting container 111 passes through the interior channel 141 and opening 115.

In the illustrated embodiment, interior channel 141 does not have a substantially uniform diameter. As shown in FIG. 4, channel 141 has a lower portion with first diameter $D_1$ and an upper portion with a second diameter $D_2$, where $D_1$ and $D_2$ are not substantially equal. In an alternate embodiment, the diameter of interior channel 141 is uniform throughout interior channel 141.

Insert 119 (FIG. 6) is coupled to interior channel 141 as shown in FIG. 5. Insert 119 includes a valve 121, valve spray hole 122, and a body 123 positioned along the perimeter of valve 121. Body 123 fits within nozzle 105 such that the diameter of valve 121 is less than D1. In other words, body 123 fits within nozzle 105 such that valve 121 is in direct, fluid communication with interior channel 141 as shown in FIG. 4. Body 123 frictionally engages with interior channel 141 to hold insert 119 in place so that valve 121 can selectively allow liquid to exit wound irrigation device 100 during operation as described in further detail below. In the illustrated embodiment, insert 119 is a single part that creates a fluid tight seal with interior channel 141 of nozzle 105 (FIG. 5). However, it is contemplated that in alternative embodiments, insert 119 can comprise more than one discrete, interfitting part.

Valve 121 selectively allows liquid to exit container 111 when a certain amount of pressure is applied to container 111. As the pressure on container 111 is increased, the pressure exerted on valve 121 increases as well. Once sufficient pressure is applied on container 111, valve 121 opens as discussed further herein and interior channel 141 and opening 115 are in fluid communication with the interior of container 111 thereby allowing liquid to pass through interior channel 141 and exit wound irrigation device 100. In one embodiment, the amount of pressure needed to be applied on wound irrigation device 100 to dispense liquid from opening 115 is between 1.5-10 psi. However, it is contemplated that other suitable pressures can be required when operating wound irrigation device 100 and 200 (as discussed further herein).

Nozzle assembly 110 further includes a spacer 107 coupled to a portion of nozzle assembly 110 as shown in FIG. 4. In alternate embodiments, spacer 107 may be integrally formed with nozzle 105. Spacer 107 is sized and configured such that the inner diameter of spacer 107 is substantially the same as the outer diameter of nozzle 105. By having the same diameter as nozzle 105, spacer 107 frictionally engages with a portion of nozzle 105 that interfaces with container 111. In an alternate embodiment, spacer 107 is coupled to nozzle 105 by fasteners (e.g. screws), couplers (e.g. pins), or adhesives (e.g. glue). When coupled to the portion of nozzle 105, spacer 107 extends outwardly and away from nozzle 105. When storing wound irrigation device 100, wound irrigation device 100 is in a flat configuration, and the outer edge of spacer 107 prevents guard 103 from interfering with interior channel 141 and opening 115. In the illustrative embodiment, spacer 107 is shown as a ring. However, it is contemplated that in alternative embodiments, spacer 107 may include other shapes such as a cube or pyramid as long as the shape of spacer 107 corresponds with the shape of nozzle 105.

Similarly, in the illustrative embodiment, nozzle 105 is shown as having a frustoconical shape. However, it is contemplated that in alternate embodiments, nozzle 105 may include other shapes such as a rectangular prism, a cube, a cylinder, etc.

Nozzle assembly 110 is assembled by coupling insert 119 to the bottom portion of interior channel 141. As described above, body 123 of insert 119 has substantially the same diameter as interior channel 141 allowing for insert 119 and interior channel 141 to frictionally engage with each other. When insert 119 is coupled to interior channel 141, valve 121 is in fluid communication with interior channel 141 and container 111 to selectively allow liquid from the interior of container 111 to exit opening 115 through interior channel 141. Once insert 119 is engaged with interior channel 141, spacer 107 is moved downwardly along the outer surface of nozzle 105 until the outer surface of nozzle 105 frictionally engages with spacer 107.

Figure 12:
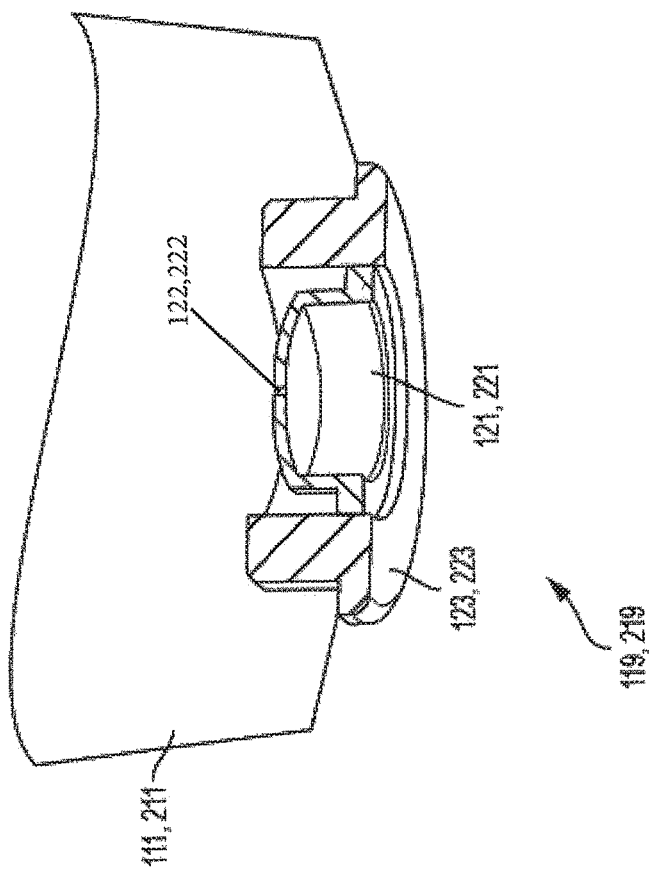
FIG. 12 is a partial sectional view of the insert of FIG. 11 when the insert is in a relaxed state.

In operation, wound irrigation device 100 is obtained as assembled as shown in FIG. 1 or assembled in the manner described above. Liquid is inserted into container 111 through valve 113. Once liquid is inserted, wound irrigation device 100 is inverted such that nozzle assembly 110 is pointed toward a surface generally indicated as 124 onto which the liquid inside container 111 may be applied. At this point, liquid in container 111 does not exit container 111 through openings 109 and 115. Liquid does not exit opening 109 because of valve 113 as discussed earlier. Liquid also does not exit through opening 115 because insert 119 is in a relaxed state (FIG. 12), where valve 121 is seated within body 123 and valve spray hole 122 is closed.

Figure 13:
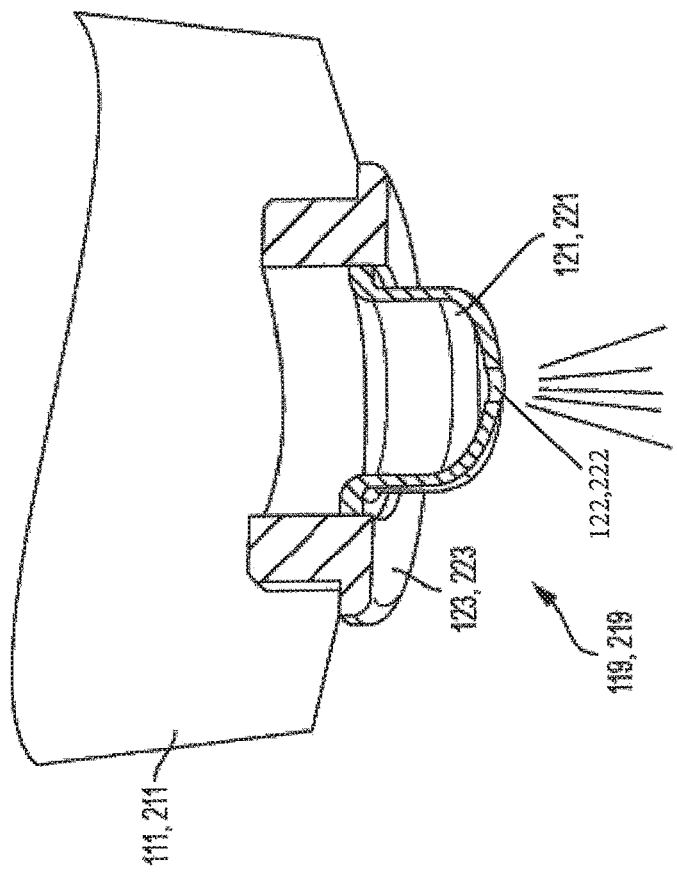
FIG. 13 is a partial sectional view of the insert of FIG. 11 when the insert is in a deployed spray state.

To apply liquid onto surface 124, pressure is applied to the outer surface of container 111. In one exemplary embodiment, a user's hand applies pressure to the outer surface of container 111. In an alternate embodiment, a separate device may be used to apply pressure onto container 111. As pressure inside container 111 increases, pressure is applied to valve 121 until insert 119 is in a deployed spray state (FIG. 13), where valve 121 moves in the direction of liquid flow and extends outwardly beyond body 123, and valve spray hole 122 is stretched open to permit liquid flow from container 111 through valve spray hole 122.

When pressure is no longer applied onto container 111, insert 119 returns to the relaxed state (FIG. 12), where valve 121 returns to its position within body 123 and valve spray hole 122 is compressed such that valve spray hole 122 is closed, thereby preventing liquid from flowing out of container 111. This mechanism allows the user to have control of the flow rate and pressure of liquid exiting container 111.

FIGS. 8-11 show another embodiment of wound irrigation device 100, in the form of wound irrigation device 200. Wound irrigation device 200 utilizes similar design features and operational principles as wound irrigation device 100 described above, and corresponding structures and features of wound irrigation device 200 retain the corresponding reference numerals of wound irrigation device 100, increased by 100. However, wound irrigation device 200 includes a single opening 215 and an alternate nozzle assembly 210 configuration as described below.

Referring to FIGS. 8-11, wound irrigation device 200 includes container 211 with opening 215 positioned along an outer surface of container 211. Nozzle assembly 210 is removably coupled to opening 215 of container 211 and comprises a nozzle 201 and a lid 205. Lid 205 and nozzle 201 are coupled to each other. In the illustrated embodiment, nozzle 201 and lid 205 are coupled together by a hinge mechanism 202. However, it is contemplated that nozzle 201 and lid 205 can be coupled together by other means, e.g., screws, bolts, pins, etc. Nozzle 201 is coupled to opening 215 and has a diameter that is substantially the same as the diameter of opening 215. In an alternate embodiment, nozzle 201 is integrally formed with container 211.

Similar to container 111 of wound irrigation device 100, container 211 may be made of a flexible material such that container 211 can be molded into different configurations to achieve greater storage capacity. Each container 211 of a plurality of containers 211 can be flattened out or collapsed such that containers 211 can be stacked on each other. In such a configuration, a greater number of containers 211 can be stored per unit area of storage. This is spatially more efficient as compared to prior more rigid embodiments of a wound irrigation device in which more rigid containers (e.g. bottles) are used. In one embodiment, container 211 is made from Bis(2-ethylhexyl)benzene-1,2-dicarboxylate (DEHP). In an alternate embodiment, container 211 may be made from PVC, rubber, or other suitable materials. In an alternate embodiment, container 211 can hold at least 250 cubic centimeters of liquid.

Similar to container 111, container 211 includes a self-standing base 245 and a gusset 243. As liquid enters container 211, container 211 expands, and gusset 243 and base 245 provide a foundation to container 211 such that container 211 can stand upright on its own.

Figure 8:
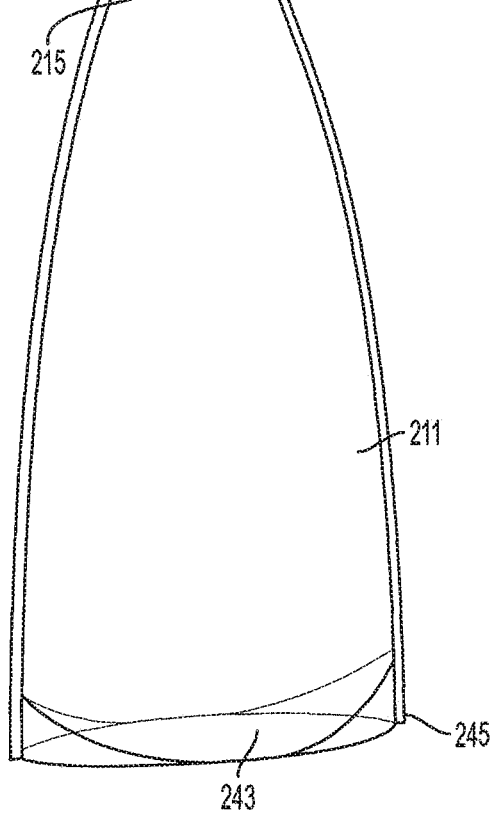
FIG. 8 is a perspective view of a second embodiment of a wound irrigation device.
Figure 9:
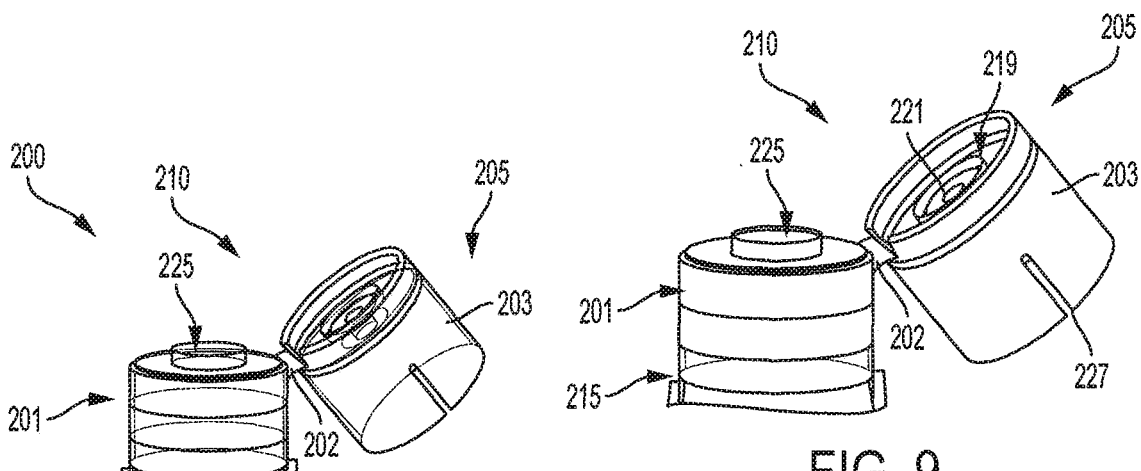
FIG. 9 is a perspective view of a hinge cap in an open configuration with the wound irrigation device of FIG. 8.

Nozzle 201 further includes an opening 225 disposed along the upper surface of nozzle 201. Opening 225 allows for the interior of container 211 to be in fluid communication with the ambient air when nozzle assembly 210 is in an open configuration as shown in FIG. 8 and described in further detail below. In the illustrated embodiment, opening 225 has a smaller diameter than the diameter of nozzle 201 and opening 215. However, it is contemplated that opening 225 can have a diameter that is substantially equal to the diameter of nozzle 201. Moreover, opening 225 and opening 215 share a common central axis, i.e. they are coaxial.

Lid 205 is coupled to nozzle 201. Lid 205 includes insert 219 and guard 203. Insert 219 is positioned along a lower surface of lid 205 such that insert 219 is in substantial alignment with opening 225 along the upper surface of nozzle 201 when nozzle assembly 210 is in a closed configuration. In the closed configuration, lid 205 engages with nozzle 201 and body 223 of insert 219 frictionally engages with the rim of opening 225 such that a fluid tight seal is formed between insert 219 and the rim of opening 225. An interior channel 241 through which liquid can flow is also defined in the closed configuration. In the illustrated embodiment, insert 219 and opening 225 have diameters that are substantially equal to provide a fluid tight seal for wound irrigation device 200. In an alternate embodiment, insert 219 and opening 225 do not have substantially the same diameter, but other components are included to provide a fluid tight seal at the interface of insert 219 and opening 225.

Insert 219 includes a valve 221 and a valve spray hole 222 configured to selectively allow fluid inside container 211 to exit opening 215 via interior channel 241. Valve 221 is configured to allow liquid to exit container 211 when a requisite amount of pressure is exerted on container 211. In one embodiment, the requisite amount of pressure needed to be applied on wound irrigation device 100 to dispense liquid is below 1.5-10 psi. However, it is contemplated that other suitable pressures can be required when operating wound irrigation device 200.

Nozzle assembly 210 further includes guard 203 with a slot 227 integrally formed therein. Slot 227 acts as a relief passage to discharge fluid, debris, pathogens, bodily fluids, etc., which may be dispersed from the cavity of the wound if such objects come into contact with nozzle assembly 210, from guard 203.

Guard 203 is coupled to an upper surface of lid 205 and extends outwardly from lid 205 to extend beyond opening 225. Guard 203 prevents liquids, bodily fluids, or other debris from contacting and damaging lid 205 and nozzle assembly 210 while permitting liquid inside container 211 to be used for irrigating a wound. In one embodiment, guard 203 is integrally formed with lid 205.

In the illustrated embodiment, guard 203 is shown to have substantially the same shape as lid 205 as both guard 203 and lid 205 are substantially cylindrical. However, it is contemplated that in alternative embodiments, guard 203 can take the form of a shape that is substantially different from lid 205 (e.g., frustoconical).

Figure 10:
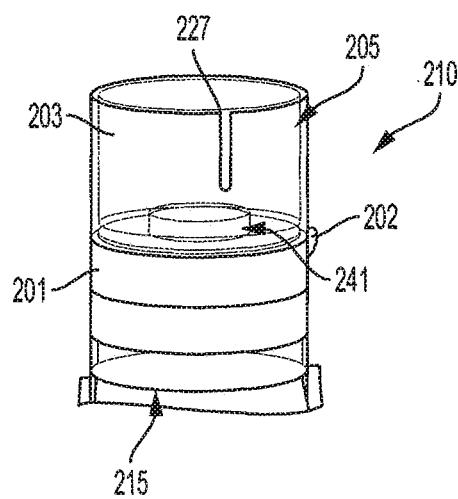
FIG. 10 is a perspective view of a hinge cap in a closed configuration with the wound irrigation device of FIG. 8.
Figure 11:
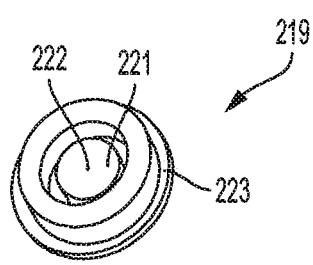
FIG. 11 is a perspective view of an insert that is incorporated into the hinge cup of FIGS. 9 and 10 of the wound irrigation device of FIG. 8.

Liquid is inserted into container 211 via opening 225. Once an adequate amount of liquid is within container 211, wound irrigation device 200 is moved into its closed configuration where nozzle assembly 210 is coupled to nozzle 201 and insert 219 is in substantial alignment with opening 225 along the upper surface of nozzle 201 as shown in FIG. 10. Insert 219 engages with opening 225 such that a fluid tight seal is formed, and valve 221 operates to selectively allow liquid to exit container 211.

To operate wound irrigation device 200, wound irrigation device 200 transitions from the closed configuration to an open configuration where nozzle 201 is coupled to opening 215, but lid 205 is decoupled from nozzle 201. Wound irrigation device 200 is then inverted such that container 211 is disposed above nozzle assembly 210, and nozzle assembly 210 is pointed towards a surface generally indicated as 224 (FIGS. 12 and 13) onto which liquid is to be applied. To apply liquid onto surface 224, sufficient pressure is applied to container 211 such that valve 221 moves from within body 223 in the relaxed state (FIG. 12) to the deployed spray state (FIG. 13), where valve 221 moves in the direction of liquid flow and extends outwardly and valve spray hole 222 is stretched open to permit liquid flow from container 211 through valve spray hole 222. When adequate pressure is no longer applied to container 211, insert 219 returns to the relaxed stated (FIG. 12), where valve 221 returns to its position within body 223 and valve spray hole 222 is compressed such that valve spray hole 222 is closed, thereby preventing liquid from flowing out of container 211.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A one-piece wound irrigation device, the device comprising:
    a flexible container for containing a treatment liquid for irrigation of wounds, the container having an inner compartment, an outer surface, a container opening having a diameter and being positioned along the outer surface of the container, a gusset positioned within the inner compartment, and a self-standing base, the container having a collapsed configuration and an expanded configuration;
    a nozzle integrally formed with the container opposite the gusset and the self-standing base, the nozzle having an upper surface and a nozzle opening having a diameter, the nozzle opening being surrounded by a rim that extends outwardly from the upper surface of the nozzle and defines a first annular-shaped sealing surface that is spaced from the upper surface of the nozzle in an axial direction of the nozzle, wherein the diameter of the nozzle opening is smaller than the diameter of the container opening and the container opening and the nozzle opening share a common central axis; and
    a lid coupled to the nozzle with a hinge mechanism about which the lid pivots between an open position and a closed position, the lid comprising;
        a lower surface that faces the upper surface of the nozzle when the lid is in the closed position;
        an insert including an insert body, a valve that is surrounded by the insert body and transitions between a relaxed state and a deployed spray state, and a valve spray hole within the valve, the insert body extending outwardly from the lower surface of the lid and defining a second annular-shaped sealing surface that is spaced from the lower surface of the lid in an axial direction of the lid and is complementary to the first annular-shaped sealing surface of the rim of the nozzle, an interior channel within the lid for receiving the treatment liquid from the container through the nozzle opening, and a cylindrical guard having an outer rim that extends outwardly beyond the insert and at least one slot in the outer rim of the cylindrical guard as a relief passage for the treatment liquid within the interior channel;

wherein when the lid is in the open position, the insert and the valve thereof are not aligned with the nozzle opening, the second annular-shaped sealing surface of the insert body is not engaged with the first annular-shaped sealing surface of the rim of the nozzle, the valve spray hole does not fluidically communicate with the nozzle opening, the inner compartment can receive the treatment liquid through the nozzle opening to be filled by a user before operating the wound irrigation device wherein filling the inner compartment moves the flexible container from the collapsed configuration to the expanded configuration;

wherein when the lid is pivoted about the hinge mechanism from the open position to the closed position, the insert and the valve thereof are aligned with the nozzle opening, the second annular-shaped sealing surface of the insert body engaging the first annular-shaped sealing surface of the rim of the nozzle to form a fluid tight seal therebetween, and the valve spray hole fluidically communicates with the nozzle opening;

wherein when the valve is in the relaxed state, the valve spray hole is closed and the treatment liquid within the inner compartment does not flow from the container through the valve spray hole;

wherein when the valve is in the deployed spray state, the valve extends outwardly beyond the insert body and the valve spray hole opens and the treatment liquid flows from the container through the valve spray hole;

wherein the wound irrigation device is a one-piece, self-contained system; and wherein when the container is in the collapsed configuration, a plurality of containers can be stacked on each other.

2. The one-piece wound irrigation device according to claim 1, wherein the container holds at least 250 cubic centimeters of water.

3. The one-piece wound irrigation device according to claim 1, wherein an inward pressure exerted on the outer surface of the container to expel water is between 1 and 10 psi.

4. The one-piece wound irrigation device according to claim 1, wherein the inner compartment of the container is filled with the treatment liquid.

5. The one-piece wound irrigation device according to claim 1, wherein the inner compartment of the container is empty.

6. The one-piece wound irrigation device according to claim 1, wherein the device includes only one valve spray hole.

7. The one-piece wound irrigation device according to claim 1, wherein the cylindrical guard is not removable from the device.

8. The one-piece wound irrigation device according to claim 1, wherein in the collapsed configuration, the gusset has a singular line fold.

9. The one-piece wound irrigation device according to claim 1, wherein the gusset is a bottom gusset.

10. The one-piece wound irrigation device according to claim 1, wherein when the valve is in the deployed spray state, the flow of the treatment liquid from the container through the valve spray hole is unobstructed.

11. The one-piece wound irrigation device according to claim 1, wherein the valve spray hole is equidistant from the outer rim of the cylindrical guard.

12. The one-piece wound irrigation device according to claim 4, wherein the treatment liquid is potable water.

13. The one-piece wound irrigation device according to claim 1, wherein the gusset is a single gusset.

14. The one-piece wound irrigation device according to claim 1, wherein the one-piece wound irrigation device is a single-use device.

15. The one-piece wound irrigation device according to claim 1, wherein the valve spray hole is a single valve spray hole.

* * * * *